United States Patent [19]

Cox

[11] Patent Number: 4,561,163
[45] Date of Patent: Dec. 31, 1985

[54] FITTING DOCTOR BLADES

[76] Inventor: Norman V. Cox, 43 W. Valley Rd., Hemel Hempstead, Hertfordshire, England

[21] Appl. No.: 495,343
[22] PCT Filed: Aug. 13, 1982
[86] PCT No.: PCT/GB82/00252
§ 371 Date: Apr. 18, 1983
§ 102(e) Date: Apr. 18, 1983
[87] PCT Pub. No.: WO83/00655
PCT Pub. Date: Mar. 3, 1983

[30] Foreign Application Priority Data

Aug. 18, 1981 [GB] United Kingdom ............... 8125242

[51] Int. Cl.⁴ ................................................ B23Q 3/00
[52] U.S. Cl. .................................. 29/464; 248/316.4; 269/160; 269/243; 269/246
[58] Field of Search ............. 29/464; 403/312, 373; 248/316.4, 489; 269/160, 243, 246

[56] References Cited

U.S. PATENT DOCUMENTS 4,323,262 4/1982 Arenhold .................. 403/312 X

FOREIGN PATENT DOCUMENTS 2709194 7/1978 Fed. Rep. of Germany .
998737 7/1965 United Kingdom .

Primary Examiner—Howard N. Goldberg
Assistant Examiner—Timothy V. Eley
Attorney, Agent, or Firm—Keil & Weinkauf

[57] ABSTRACT

For fitting a strip-like flexible metal doctor blade (4) into the usual clamp means (1, 2) of a rotary printing machine there is used a guide (5) having first and second stop surfaces (5a, 5b) which are linear and parallel, and are spaced by the extent by which it is desired that the blade (4) shall eventually protrude from the clamp means (1, 2). The blade (4) is abutted against one stop surface (5a), and is then secured in the guide (5). The guide (5), with the blade (4) in it, is then moved to cause the second stop surface (5b) to abut against the clamp means (1), with the protruding portion of the blade (4) inserted into the clamp means (1, 2). The clamp means (1, 2) are tightened onto the blade (4), and the guide (5) is removed. For a blade (4) consisting of two strip-like parts placed face to face, the guide (5) is provided with a step. One blade part is abutted against the stop surface, and the other blade part is abutted against the step.

6 Claims, 6 Drawing Figures

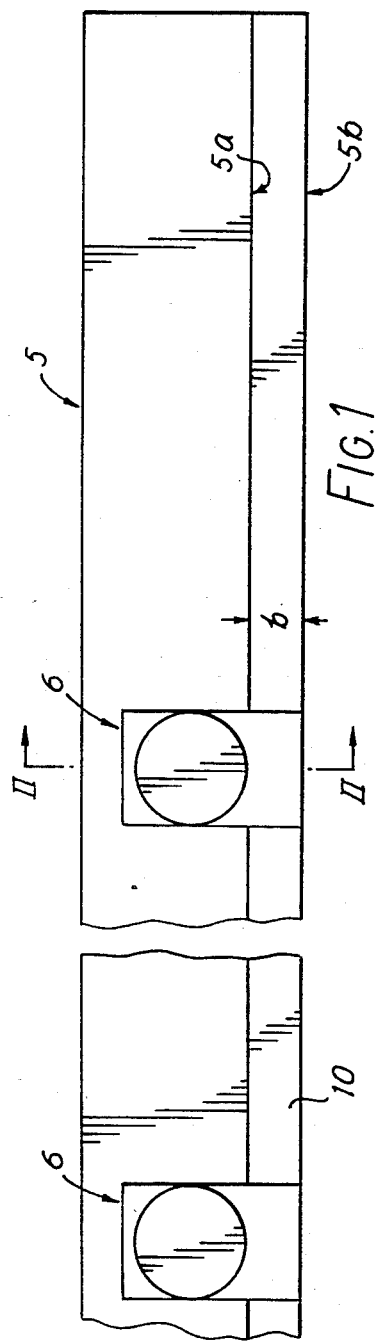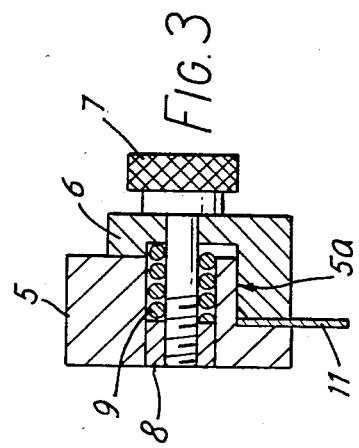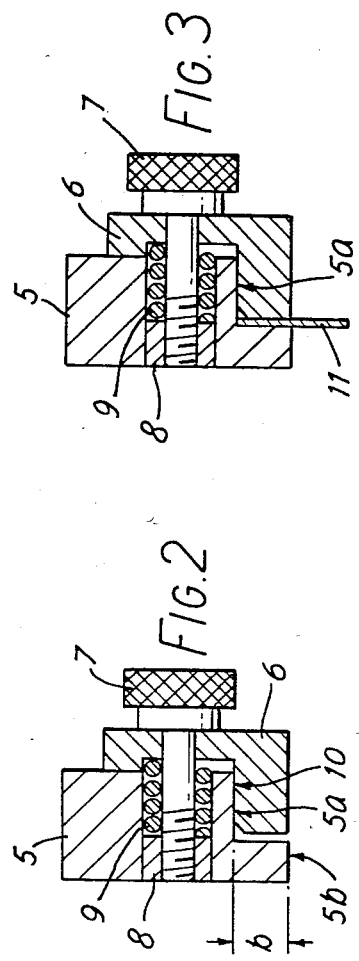

FITTING DOCTOR BLADES

This invention relates to the fitting of doctor blades in rotary printing machines. Such blades are commonly formed of relatively thin and flexible strip steel which is inserted into a blade holder in the machine.

A problem in the fitting of a new doctor blade to the blade holder of the machine is that of ensuring that the edge of the blade presented towards the circumference of the printing cylinder is precisely linear both axially and radially with respect to the cylinder, and that the extent of projection of the blade from the blade holder is constant along all of the length of the blade.

It is relatively easy to cause misalignment and even buckling of the relatively flimsy blade, in its own plane and/or normal to its own plane, and much skilled labour and time is currently occupied in ensuring that the blade, once fitted, has its scraping edge perfectly true.

It is accordingly the object of the present invention to provide a method, and a guide means for use in carrying out the method, which permit the fitting of a doctor blade strip into the usual holder in a simple manner with complete accuracy, and without requiring subsequent grinding or other trueing operating on the blade.

According to the present invention a method of fitting a strip-like doctor blade into a clamp means of a printing machine comprises the steps of:

(i) inserting the blade into a guide means and abutting a first edge of the blade, which will eventually be exposed towards the cylinder, against a first linear stop surface of the guide means.

(ii) applying force to the blade to hold it firmly in that abutted condition, (iii) abutting a second linear stop surface of the guide means, parallel to the first stop surface and spaced from the first stop surface in the direction towards the second edge of the blade, against the clamp means with a portion of the blade being inserted into the clamp means, (iv) tightening the clamp means onto the blade, and (v) removing the guide from the blade.

As the first and second stop surfaces of the guide are parallel, and the eventual scraping surface of the blade abuts one of them, and the other of them abuts the clamp means, the above series of steps ensures that the portion of blade which is eventually exposed from the clamp means is both linear and of the same extent of protrusion along the entire length. The distance of which the first and second stop surfaces are spaced is preferably made the same as the extent to which the blade is desired to protrude from the clamp means.

The application of force to the blade is preferably by use of tightening means of the guide. e.g. tightening of releasable holder means of the guide.

A guide for use in carrying out the method set forth above comprises an elongated body having along its length a first linear stop surface, to be abutted by a first edge of the blade, a second linear stop surface parallel to said first stop surface and spaced therefrom in the direction towards the second edge of the blade when so abutted, and means for applying force to the blade to hold it in abutted condition.

The means for applying force may be a plurality of holders positioned at intervals along the elongated body and capable of being released and tightened onto the blade.

In a preferred embodiment, the elongated body is a bar having a recess bounded by two surfaces forming an "L" shape, one surface forming the first stop surface, and the other such surface receiving the blade against it and serving in the application of force to the blade. By way of example the holders may be substantially L-shaped elements having one leg extending into said recess to hold the blade against said other surface, and the other leg provided with means for tightening onto the elongated body.

In a preferred modification, said other surface is stepped, thereby to permit one strip of a two-part blade to abut against the first stop surface, and other strip of the two-part blade to abut against the step.

In order that the nature of the invention may be readily ascertained, an example of the method of fitting a doctor blade into the usual clamp means of a printing machine, and a guide for use in carrying out that method, are hereinafter particularly described with reference to the figures of the accompanying drawings, wherein:

FIG. 1 is a partial front elevation of the guide;

FIG. 2 is a section taken on the line II—II of FIG. 1;

FIG. 3 is a section corresponding to that of FIG. 2, but showing a doctor blade strip clamped in the guide;

Figure 4:
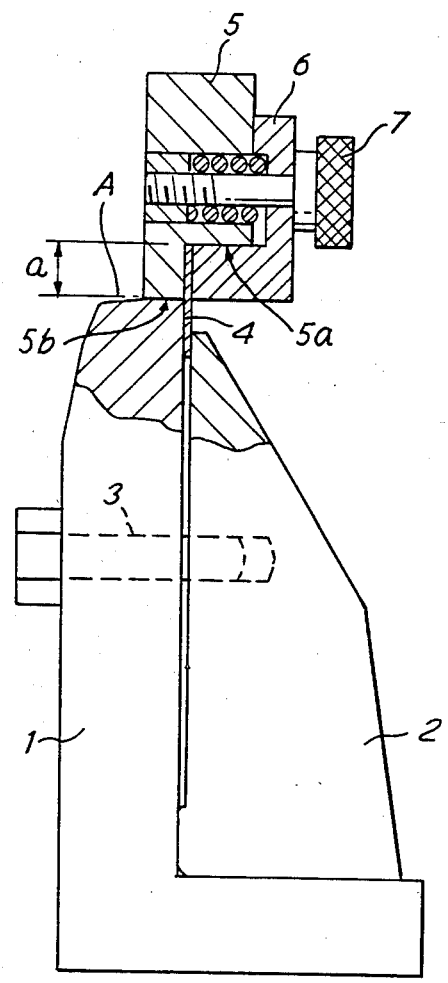
FIG. 4 is a section showing the guide, with blade strip clamped therein, applied to the usual clamp means of a printing machine.

Referring firstly to FIG. 4, the usual clamp means of a printing machine are represented here by an L-shaped fixed clamp member 1, and a movable clamp member 2 which can seat into the member 1 and which can be tightened by means of a plurality of tightening bolts 3.

It is necessary, in practical operation of the printing machine, to place a blade 4 between the respective upper edges of the members 1 and 2, and then to clamp it firmly, with the dimension "a" (the protrusion of the blade from the clamping means) being not only correct to an extremely high limit of accuracy, but being also constant along all of the length of the clamping means, perhaps several meters. This has hitherto been carried out by clamping a length of strip 4 in the clamping means 1,2 with the dimension "a" roughly correct and roughly the same along all of the length of the clamping means, then placing the entire clamping means (which had to be removed from the printing machine for the purpose) in a grinding jig, setting up the end face "A" so as to be exactly parallel to the grinding means, then grinding the exposed portion of the blade 4, and then removing the burrs resulting from the grinding, after which the clamping means had to be re-assembled into the printing machine. The result of this procedure was that a great deal of time and labour had to be used, whereas the end result was not alway satisfactory because the de-burring of the blade after grinding often resulted in loss of edge and other malformation, thereby materially reducing the useful life of the blade.

The method of the present invention utilises a guide shown in FIGS. 1 and 2. The guide consists of an elongated bar 5 of a length somewhat greater than the length of the doctor blade to be fitted, and having a considerable cross-sectional area for stability in use. The length might be, for example, a little over two meters. At a number of points along its length, e.g. at ten points at even spacing, there are positioned respective holders 6 each of which can tightened onto the bar 5 by means of a respective knurled screw 7 threaded into a sleeve 8 secured in the bar 5. A coiled compression spring 9 is seated between the bar 5 and the holder 6 to urge the holder outwardly when the screw 7 is untightened. The holder 6 is in the form of an L-shaped element having one leg engaged by the knurled head of the screw 7, and the other leg seated into a recess 10 which extends along the entire length of the bar 5. The bar 5 is carefully manufactured to have its surfaces 5a and 5b linear and so that the dimension "b" is constant all along the bar and is precisely the extent to which it is desired that a doctor blade shall protrude from the clamp means 1,2 of FIG. 4. Thus, the dimension "b" of the bar 5 shown in FIGS. 1 and 2 is the same as the dimension "a" shown in FIG. 4.

With the holders 6 all released, a strip of metal doctor blade 11 is inserted between the bar 5 and the holders 6, with its edge butted precisely against the first stop surface 5a. The holders 6 are all tightened to grip the blade 11 firmly onto the bar 5. The bar 5 is then placed in position onto the clamp means 1,2 of the printing machine, e.g. while the clamping means remain in situ in the machine, with the second stop surface 5b abutting the clamp element 1, as shown in FIG. 4. The clamping means are then tightened onto the blade by tightening all of the screw 3, whereafter the holders 6 can then be released to permit the bar 5 to be removed. This leaves the doctor blade strip 11 protruding from the clamping means by exactly the extent "a", and the extent of protrusion is constant along all of the length of the clamping means. Thus, the blade strip 11 does not need adjustment or grinding after insertion, and its exposed edge needs no de-burring or other subsequent operation, so that the length of useful life of the doctor blade is much enhanced.

Figure 5:
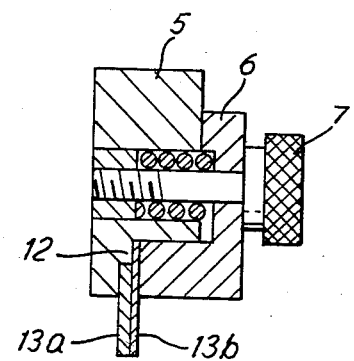
FIG. 5 is a section, similar to that of FIG. 3, but wherein the single blade strip is replaced by two strips placed face to face.
Figure 6:
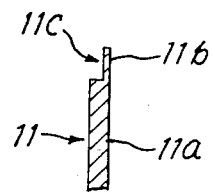
FIG. 6 is a cross-section to show part of a known type of blade having a thinned edge portion.

It can be a considerable advantage in practical use of such doctor blades if the blade strip has a relatively thick body portion 11a surmounted by a relatively much thinner edge portion 11b (see FIG. 6). Hitherto, such blades have been obtained by taking a strip of blade material and taking away the zone 11c, which makes the blades extremely costly to manufacture. The guide means of the present invention can be used in such a manner as to permit a similar effect, to that of the blade of FIG. 6, to be obtained in a much simpler manner and at a very much reduced cost. The bar 5 is modified by forming, in one of the two surfaces bounding its recess 10, a step formation 12 (see FIG. 5). The procedure described above is carried out in exactly the same manner, but instead of the single strip of blade material 11 there are used two strips 13a and 13b placed face to face. The strip 13a is of the greater thickness corresponding to the portion 11a in FIG. 6, and the strip 13b is of the much lesser thickness corresponding to 11b in FIG. 6. The two strips 13a, 13b are each butted fully up against their respective stop surfaces of the bar 5, both of the strips are inserted into, and clamped by, the clamping means 1,2, and the resultant is a (two-part) blade which protrudes from the clamping means by exactly the correct amount, and which was effectively a thin edge portion of 13b supported by the thicker body portion 13a.

In these manners of use, the bar 5 and the holders 6 can either abut directly onto the material of the blade strip, or intermediate buffer material, e.g. a strip or strips of plastics material may be included.

It will be appreciated that the "second stop surface" to abut the clamp means need not be a continuous surface, but could be two or more spaced abutments. Similarly, the first stop surface need not be interrupted.

I claim:

1. A guide means, for use in fitting a strip-like doctor blade, having first and second parallel edges, into clamp means of a printing machine, said guide means including:
    (i) an elongated guide member with a first linear stop surface to be abutted by said first edge of the blade, a second linear stop surface parallel to and spaced from said first stop surface, and a plane blade gripping face disposed between said first and second linear stop surfaces,
    (ii) holding means movable with respect to the guide member and having a plane blade gripping face movable towards and away from the plane blade gripping face of the guide member for holding the blade, wherein the holding means comprises a plurality of holders disposed at intervals along the guide member, each holder being connected to the guide member by a respective screw engaged with the holder and threaded into the guide member, such that rotation of the screw causes the plane blade gripping face of the holder to be moved parallel to the axis of the screw towards or away from the parallel plane blade gripping face of the guide member in a direction normal to those plane faces.

2. A guide means, as set forth in claim 1, wherein the elongated guide member is a bar having a recess bounded by two surfaces forming an "L" shape, one such surface constituting said first linear stop surface, and the other such surface constituting said plane blade gripping face of the guide member.

3. A guide means, as set forth in claim 2, wherein said holders are substantially L-shaped elements having one leg extending into said recess and providing said plane blade gripping face of the holder, and having said screw engaged with the other leg.

4. A guide means, as set forth in claim 1, wherein said guide member includes a stop element, spaced from said first stop surface, for abutment by an edge of a second part of a two part blade.

5. In a method of fitting a strip-like doctor blade, having first and second parallel edges, into the clamp means of a printing machine, including the steps of,
    (i) inserting the blade into guide means comprising an elongated guide member having a first linear stop surface and a second linear stop surface parallel to and spaced from the first stop surface, and abutting a first edge of the blade, which will eventually be exposed towards a cylinder of the printing machine, against said first stop surface,
    (ii) holding the blade firmly against said guide member in that abutted condition,
    (iii) abutting the second linear stop surface against the clamp means with a portion of the blade inserted into the clamp means,
    (iv) tightening the clamp means onto the blade, and
    (v) releasing the holding of the blade and removing the guide means off the blade, the improvement comprising: holding the blade against the guide member and releasing the holding of the blade by rotating screws, each engaged with a respective one of a plurality of holders and threaded into the guide member, such that a plane blade gripping face of each holder is moved parallel to the axis of the screw towards or away from a parallel plane blade gripping face of the guide member in a direction normal to those plane faces.

6. In a method of fitting a two-part strip-like doctor blade, having a first edge on one said blade part and a second parallel edge on the other said blade part, into the clamp means of a printing machine, including the steps of, (i) inserting the two parts of the blade into a guide means, said guide means comprising an elongated guide member having a first linear stop surface, a second linear stop surface parallel to and spaced from said first stop surface, and a stop element spaced between said first and second stop surfaces, (ii) abutting said first edge, of said one blade part, which will eventually be exposed towards a cylinder of the printing machine, against said first stop surface, and abutting said second edge of the other blade part against said stop element, (iii) holding the blade parts firmly against each other and against the guide member in that abutted condition, (iv) abutting the second linear stop surface against the clamp means with a portion of the blade parts inserted into the clamp means, (v) tightening the clamp means onto the blade parts, and (vi) releasing the holding of the blade parts and removing the guide means off the blade parts, the improvement comprising:

holding the blade parts firmly against each other and against the guide member, and releasing the holding of the blade parts by rotating screws, each engaged with a respective one of a plurality of holders and threaded into the guide member, such that a plane blade gripping face of each holder is moved parallel to the axis of the screw towards or away from a parallel plane blade gripping face of the guide member in a direction normal to those place faces.

* * * * *